United States Patent [19]

Keane, II

[11] Patent Number: 5,215,750
[45] Date of Patent: Jun. 1, 1993

[54] L-GLUTAMINE AND VITAMIN-CONTAINING COMPOSITIONS EFFECTIVE FOR INDUCING WEIGHT LOSS AND FOR WEIGHT CONTROL

[76] Inventor: Michael A. Keane, II, 38 Port Lewes, Lewes, Del. 19958

[21] Appl. No.: 754,952

[22] Filed: Sep. 4, 1991

[51] Int. Cl.$^5$ .......................... A61K 9/08; A61K 9/10; A61K 9/20; A61K 9/48
[52] U.S. Cl. ..................................... 424/440; 424/439; 424/441; 424/451; 424/464; 424/602; 424/630; 424/639; 424/641; 424/646; 424/648; 424/667; 424/692; 424/702; 426/73; 426/74; 426/656; 514/909; 514/937
[58] Field of Search ............... 424/439, 440, 602, 630, 424/639, 641, 646, 648, 667, 692, 702; 514/909, 910

[56] References Cited

U.S. PATENT DOCUMENTS 4,298,601 11/1981 Howard ............................. 424/642
4,687,782 8/1987 Brantman ........................... 514/562

Primary Examiner—Thurman K. Page
Assistant Examiner—James M. Spear

[57] ABSTRACT

Compositions comprising L-glutamine in combination with vitamins, minerals, choline, and flavonoids are disclosed. Such compositions can be administered to effect weight reduction, or to aid in weight control.

15 Claims, No Drawings

L-GLUTAMINE AND VITAMIN-CONTAINING COMPOSITIONS EFFECTIVE FOR INDUCING WEIGHT LOSS AND FOR WEIGHT CONTROL

BACKGROUND OF THE INVENTION

Field of the Invention

The present invention relates to the use of the amino acid glutamine, in conjunction with vitamins and various minerals, as an aid in effecting weight loss, and in achieving weight control.

Description of Related Art

The amino acid L-glutamine is involved in the synthesis of γ-aminobutyric acid (GABA), a known inhibitory brain neurotransmitter. Increases in GABA result in reduced anxiety and alcohol consumption.

Neurotransmitters and neuromodulators are known to stimulate or inhibit eating behavior (Blum et al. (1990) *Curr. Ther. Res.* 48(2):217-233). While the specific causes of uncontrollable food ingestive behavior, especially for carbohydrates, are not completely understood, it is believed that such compulsive behavior is a product of genetic predisposition and environmental insult factors. These factors are believed to operate through particular alterations in the neurochemical balance of the brain, inducing compulsive-seeking behavior.

Multiple brain neurotransmitters have been hypothesized to play a significant role in the control of food intake, appetite for specific macronutrients, and patterns of meal-taking behavior. Neurotransmitters such as brain monoamines and neuropeptides, which operate at neuronal centers which are part of a complex network known as the mesolimbic reward system, have been implicated as playing a role in the control of normal eating behavior (Leibowitz (1986) *Federation Proc.* 45: 1396; Wise (1983) in Smith et al., eds., *The Neurobiology of Opiate Reward Processes,* Elsevier Biomedical, Amsterdam, pages 361-402). Via analysis of cerebrospinal fluid, it has been possible to associate abnormal eating patterns in both humans and animals with specific disturbances in brain neurochemical function (Kaye et al. (1984) *Am. J. Psychiatry* 141:1598; Kaye et al. (1985) *Psychiatry Res.* 14:333).

The eating-inhibitory brain neurotransmitters include the monoamines dopamine, norepinephrine, and serotonin, as well as the gut-brain peptides cholecystokinin-8, neurotensin, calcitonin, glucagon, and corticotropin-releasing factor (summarized in Blum et al. (1990) *Curr. Ther. Res.* 48:217). The effects of these neurotransmitters on eating are characterized primarily by a specific change in macronutrient selection, rather than an increase or decrease in total food intake.

SUMMARY OF THE INVENTION

In a study of the effects of precursor amino acid loading and enkephalinase inhibition on compulsive eating and weight loss by chronic carbohydrate bingers, Blum et al. ((1990) *Curr. Ther. Res.* 48:217) demonstrated that the use of the amino acid supplement PCAL-103, an experimental variant of SAAVE ™, a product which reduces craving in alcoholics and heroin abusers, and which contains DL-phenylalanine, L-tryptophan, L-glutamine, and pyridoxal-5'-phosphate, suppressed eating behavior. Chronic carbohydrate bingers lost 2.7 times as much weight as patients who did not use PCAL-103. The apparent beneficial effects of PCAL-103 were attributed to the action of both the precursor amino acids and enkephalinase inhibition operating on mesolimbic reward circuitry. The authors pointed out that no exact mechanism of action for the neuronutrient mixture could be provided, nor could the ingredient or combination of ingredients which best suppresses carbohydrate binging be identified. The authors conjectured that a possible mechanism for the effects observed with PCAL-103 includes the restoration of deficient monoamines such as serotonin, dopamine, and epinephrine, as well as the neuropeptides methionineenkephalin and cholecystokinin-8, all of which are considered to be inhibitory eating (carbohydrate) substances influenced by either glucose or genetics.

These authors further conjectured that glucose binging is similar to other chemical dependencies such as for alcohol, cocaine, and heroin. Given the apparent effectiveness of various neuronutrients in facilitating the recovery of alcoholics and drug abusers, the authors concluded that a common mode of treatment for abuse of these diverse substances might be possible, and therefore that further research with eating-disorder patients for the development of novel therapeutic measures is warranted by the presumption that the basis of eating disorders lies in a derangement or imbalance in brain neurochemistry.

Accordingly, it is an object of the present invention to provide a composition useful for stimulating weight loss and for maintaining control of weight in mammals, including humans.

A further object of the present invention is to provide a method for stimulating weight loss, and for weight control, in mammals, including humans.

These objects and others are accomplished in accordance with the present invention by administering to a subject, including a human, a weight loss-stimulating or weight-controlling effective amount of a composition comprising L-glutamine or a physiologically acceptable salt thereof.

Further scope of the applicability of the present invention will become apparent from the detailed description provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The following detailed description of the invention is provided to aid those skilled in the art in practicing the present invention. Even so, the following detailed description of the invention should not be construed to unduly limit the present invention, as modifications and variations in the embodiments herein discussed may be made by those of ordinary skill in the art without departing from the spirit or scope of the present inventive discovery.

Compositions Containing L-Glutamine

The weight loss composition of the present invention is a formulation comprising L-glutamine in combination with vitamins, minerals, choline, and one or more flavonoids, in tablet, capsulet, lozenge, or liquid form.

L-glutamine can be formulated into a composition useful in effecting weight reduction and for effectively maintaining weight control by combining this amino acid with the following:

A vitamins
B vitamins
Biotin
Vitamin C
Choline
Vitamin D
Vitamin E
Folic Acid
Inositol
Vitamin K
Niacinamide
Pantothenic acid
Para-aminobenzoic acid
Mineral salts
Flavonoid(s)

EXAMPLE 1

Particular examples of vitamins, minerals, and flavonoids which can be included with L-glutamine in the composition of the present invention are:
Vitamin A (β-carotene)
Vitamin A (Palmitate)
Vitamin B-1 (Thiamine mononitrate)
Vitamin B-2 (Riboflavin)
Vitamin B-6 (Pyridoxine hydrochloride)
Vitamin B-12 (Cobalamin concentrate)
Biotin
Vitamin C (Ascorbic acid)
Choline (Bitartrate)
Vitamin D (Cholecalciferol)
Vitamin E (Alpha tocopherol, as D-alpha tocopheryl acetate)
Folic acid
Inositol
Vitamin K (Phylloquinone)
Niacinamide (Nicotinic acid amide)
Pantothenic acid (D-Calcium pantothenate)
Para-aminobenzoic acid
Calcium (Calcium phosphate)
Phosphorus (Calcium phosphate)
Magnesium (Magnesium oxide)
Iron (Ferrous fumarate)
Zinc (Zinc gluconate)
Copper (Copper gluconate)
Iodine (Kelp)
Manganese (Manganese gluconate)
Molybdenum (Amino acid chelate)
Chromium (Amino acid chelate)
Selenium (Sodium selenate)
Rutin

EXAMPLE 2

Formulations of the L-glutamine-containing compositions of the present invention can comprise the components set forth in Example 2 at the following dosages:

| | |
|---|---|
| L-glutamine | 500 mg to 3000 mg |
| Vitamin A (β-carotene) | 1250 I.U. to 7500 I.U. |
| Vitamin A (Palmitate) | 1250 I.U. to 7500 I.U. |
| Vitamin B-1 (Thiamine mononitrate) | 3.33 mg to 20 mg |
| Vitamin B-2 (Riboflavin) | 3.33 mg to 20 mg |
| Vitamin B-6 (Pyridoxine hydrochloride) | 5 mg to 30 mg |
| Vitamin B-12 (Cobalamin concentrate) | 15 mcg to 90 mcg |
| Biotin | 500 mcg to 3000 mcg |
| Vitamin C (Ascorbic acid) | 416.66 mg to 2500 mg |
| Choline (Bitartrate) | 83.33 mg to 500 mg |
| Vitamin D (Cholecalciferol) | 66.66 I.U. to 400 I.U. |
| Vitamin E (Alpha tocopherol, as D-alpha tocopheryl acetate | 66.66 I.U. to 400 I.U. |
| Folic acid | 66.66 mcg to 400 mcg |
| Inositol | 83.33 mg to 500 mg |
| Vitamin K (Phylloquinone) | 16.66 mcg to 100 mcg |
| Niacinamide (Nicotinic acid amide) | 33.33 mg to 200 mg |
| Pantothenic acid (D-Calcium pantothenate) | 25 mg to 150 mg |
| Para-aminobenzoic acid | 5 mg to 30 mg |
| Calcium (Calcium phosphate) | 41.66 mg to 250 mg |
| Phosphorus (Calcium phosphate) | 41.66 mg to 250 mg |
| Magnesium (Magnesium oxide) | 33.33 mg to 200 mg |
| Iron (Ferrous fumarate) | 5 mg to 30 mg |
| Zinc (Zinc gluconate) | 5 mg to 30 mg |
| Copper (Copper gluconate) | 0.33 mg to 2 mg |
| Iodine (Kelp) | 25 mcg to 150 mcg |
| Manganese (Manganese gluconate) | 1.66 mg to 10 mg |
| Molybdenum (Amino acid chelate) | 33.33 mcg to 200 mcg |
| Chromium (Amino acid chelate) | 33.33 mcg to 200 mcg |
| Selenium (Sodium selenate) | 16.66 mcg to 100 mcg |
| Rutin | 33.33 mg to 200 mg |

As will be understood by those skilled in the art, the preceding Example should not be construed as limiting the present invention, but only as being illustrative of specific chemical forms in which the components listed may be employed. Intended to be included in the present composition are those equivalents, derivatives, physiologically acceptable salts, etc. which may be employed to achieve the same effect as those illustrated above, as would be apparent to skilled workers in the art. Examples of physiologically acceptable salts of compounds which may be employed in the present invention include, for example, salts such as hydrochlorides, sulfates, phosphates, sulfamidates, acetates, lactates, tartrates, maleates, succinates, methanesulfonates, ethanesulfonates, benzenesulfonates, p-toluenesulfonates, etc.

In addition to formulation of the above composition in capsule form, said composition can also be formulated as a tablet, capsulet, lozenge, solution, emulsion, or suspension. In all cases, pharmaceutically acceptable carriers compatible with the active ingredients can be employed for the purpose of administering the present composition. In addition, the present nutrient composition may contain other active ingredients such as antimicrobial agents and other agents such as preservatives.

The present composition can be administered orally or parenterally, e.g., intramuscularly, intravenously, intraperitoneally, etc.

Use of the Composition to Effect Weight Reduction and for Weight Control

The composition of the present invention can be employed to effect weight reduction and for weight control in children and adults. It can be taken by dissolving the composition, in powder form, in water, and then drinking. When in this form, a flavoring agent can be added, for example orange flavor, to enhance the palatability thereof.

The composition of the present invention can also be formulated into a lozenge by mixing the ingredients thereof into a flavored hard candy sugar base, and then subjecting this mixture to a conventional fusion or candy molding process.

Additional formulations of the composition include capsulets, tablets, emulsions, and suspensions.

The recommended dosage of the composition of the present invention depends upon the intended effect, i.e., whether weight reduction or weight control/stabilization is desired. For the purpose of weight reduction, the recommended dosage is in the range of from about 2 to about 6 grams per day, more preferably from about 3 to about 5 grams per day, and most preferably from about 3.5 to about 4.5 grams per day. A typical dosage is 3.75 grams per day, administered in three separate portions of 1.5 grams/1.5 grams/0.75 gram over a 24 hour period. For the purpose of weight control, the recommended dosage is in the range of from about 1.5 to about 3.0 grams per day, more preferably from about 1.75 to about 2.75 grams per day, and most preferably from about 2.0 to about 2.5 grams per day. A typical dosage is 2.25 grams per day, administered in three separate portions of 0.75 gram/0.75 gram/0.75 gram over a 24 hour period.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A weight loss composition, comprising a weight-reducing effective amount of L-glutamine, and vitamins, consisting of the components listed below at the indicated dosages:

| | |
|---|---|
| L-glutamine | 500 mg to 3000 mg |
| Vitamin A (β-carotene) | 1250 I.U. To 7500 I.U. |
| Vitamin A (Palmitate) | 1250 I.U. to 7500 I.U. |
| Vitamin B-1 (Thiamine mononitrate | 3.33 mg to 20 mg |
| Vitamin B-2 (Riboflavin) | 3.33 mg to 20 mg |
| Vitamin B-6 (Pyridoxine hydrochloride | 5 mg to 30 mg |
| Vitamine B-12 (Cobalamin concentrate) | 15 mcg to 90 mcg |
| Biotin | 500 mcg to 3000 mcg |
| Vitamin C (Ascorbic acid) | 416.66 mg to 2500 mg |
| Choline (Bitartrate) | 83.33 mg to 500 mg |
| Vitamin D (Cholecalciferol) | 66.66 I.U. to 400 I.U. |
| Vitamin E (Alpha tocopherol, as D-alpha tocopheryl acetate | 66.66 I.U. to 400 I.U. |
| Folic acid | 66.66 mcg to 400 mcg |
| Inositol | 83.33 mg to 500 mg |
| Vitamin K (Phylloquinone) | 16.66 mcg to 100 mcg |
| Niacinamide (Nicotinic acid amide) | 33.33 mg to 200 mg |
| Pantothenic acid (D-Calcium pantothenate) | 25 mg to 150 mg |
| Para-aminobenzoic acid | 5 mg to 30 mg |
| Calcium (Calcium phosphate) | 41.66 mg to 250 mg |
| Phosphorous (Calcium phosphate) | 41.66 mg to 250 mg |
| Magnesium (Magnesium oxide) | 33.33 mg to 200 mg |
| *-continued* | |
| Iron (Ferrous fumarate) | 5 mg to 30 mg |
| Zinc (Zinc gluconate) | 5 mg to 30 mg |
| Copper (Copper gluconate) | 0.33 mg to 2 mg |
| Iodine (Kelp) | 25 mcg to 150 mcg |
| Manganese (Manganese gluconate) | 1.66 mg to 10 mg |
| Molybdenum (Amino acid chelate) | 33.33 mcg to 200 mcg |
| Chromium (Amino acid chelate) | 33.33 mcg to 200 mcg |
| Selenium (Sodium selenate) | 16.66 mcg to 100 mcg |
| Rutin | 33.33 mg to 200 mg |

2. The weight loss composition of claim 1, wherein said composition is in a form selected from the group consisting of a capsule, a capsulet, a tablet, a lozenge, a solution, an emulsion, and a suspension.

3. The weight loss composition of claim 1, wherein said composition is administered orally or parenterally.

4. A method of inducing weight loss in a mammal, comprising administering to said mammal a weight loss inducing effective amount of the composition of claim 1.

5. The method of claim 4, wherein said weight loss inducing effective amount is in the range of from about 2 to about 6 grams per day.

6. The method of claim 5, wherein said weight loss inducing effective amount is in the range of from about 3 to about 5 grams per day.

7. The method of claim 6, wherein said weight loss inducing effective amount is in the range of from about 3.5 to about 4.5 grams per day.

8. The method of claim 7, wherein said weight loss inducing effective amount is 3.75 grams per day.

9. The method of claim 8, wherein said weight loss inducing effective amount is administered in three separate portions of 1.5 grams/1.5 grams/0.75 gram administered over a 24 hour period.

10. A method for achieving weight control in a mammal, comprising administering to said mammal a weight control/weight stabilizing effective amount of the composition of claim 1.

11. The method of claim 10, wherein said weight control/weight stabilizing effective amount is in the range of from about 1.5 to about 3.0 grams per day.

12. The method of claim 11, wherein said weight control/weight stabilizing effective amount is in the range of from about 1.75 to about 2.75 grams per day.

13. The method of claim 12, wherein said weight control/weight stabilizing effective amount is in the range of from about 2.0 to about 2.5 grams per day.

14. The method of claim 13, wherein said weight control/weight stabilizing effective amount is 2.25 grams per day.

15. The method of claim 14, wherein said weight control/weight stabilizing effective amount is administered in three separate portions of 0.75 gram/0.75 gram/0.75 gram administered over a 24 hour period.

* * * * *